United States Patent [19]

Ashjian et al.

[11] Patent Number: 4,985,156

[45] Date of Patent: Jan. 15, 1991

[54] PRODUCTION OF BORATED ASHLESS DISPERSANTS

[75] Inventors: Henry Ashjian, E. Brunswick; Henry A. Gawel, Clark, both of N.J.

[73] Assignee: Mobil Oil Corporation, Fairfax, Va.

[21] Appl. No.: 426,610

[22] Filed: Oct. 24, 1989

[51] Int. Cl.$^5$ .......................................... C10M 139/00
[52] U.S. Cl. .............................. 252/49.6; 252/51.5 A; 548/405; 548/545; 558/291; 558/294; 585/10; 585/310
[58] Field of Search ............... 252/49.6, 51.5 A; 548/405, 545; 558/291, 294; 585/10, 310

[56] References Cited

U.S. PATENT DOCUMENTS

| | | | |
|---|---|---|---|
| 4,173,540 | 11/1979 | Lonstrup et al. | 252/49.6 |
| 4,652,387 | 3/1987 | Andress, Jr. et al. | 252/51.5 A |
| 4,689,051 | 8/1987 | Sung | 44/72 |
| 4,698,169 | 10/1987 | Andress, Jr. et al. | 252/51.5 A |
| 4,704,215 | 11/1987 | Hota et al. | 252/51.5 A |
| 4,803,004 | 2/1989 | Andress et al. | 252/51.5 A |
| 4,827,064 | 5/1989 | Wu | 585/12 |
| 4,827,073 | 5/1989 | Wu | 585/530 |

*Primary Examiner*—Margaret B. Medley
*Attorney, Agent, or Firm*—Alexander J. McKillop; Charles J. Speciale; Malcolm D. Keen

[57] ABSTRACT

A borated reaction product that is useful as a dispersancy enhancing lubricant additive. The product is produced from the maleic anhydride adduct of an olefinic alpha-olefin oligomer. The oligomer (HVI-PAO) comprises the product of the oligomerization of $C_2$ to $C_{24}$ alpha-olefin using a reduced valence state Group VIB metal as the oligomerization catalyst. This adduct of maleic anhydride and HVI-PAO is reacted with a secondary amine such as diphenylamine, an alkanol amine such as triethanolamine, and a borating agent such as boric acid or a borate ester.

20 Claims, No Drawings

PRODUCTION OF BORATED ASHLESS DISPERSANTS

FIELD OF THE INVENTION

This invention relates to a process for the production of additives useful in lubricant compositions having superior dispersant properties. More particularly, the invention relates to borated derivatives of the adducts of maleic anhydride with oligomers prepared from alpha-olefins with Group VIII metal catalyst.

CROSS-REFERENCE TO RELATED APPLICATION

This application is related to co-pending U.S. patent application Ser. No. 07/342,779, filed 25 April 1989.

BACKGROUND OF THE INVENTION

Recently, novel high viscosity index (V.I.) lubricant compositions comprising polyalpha-olefins produced with reduced chromium oligomerization catalysts have been disclosed in U.S. Pat. Nos. 4,827,064 and 4,827,073, to which reference is made for a description of these materials and of their preparation. These materials, referred to as HVI-PAO (High Viscosity Index—Poly Alpha Olefins) are made by contacting a $C_6$–$C_{20}$ 1-alkene feedstock with reduced valence state chromium oxide catalyst on porous silica support under oligomerizing conditions. The high viscosity index liquid hydrocarbon lubricants produced have branch ratios less than 0.19 and pour point below $-15°$ C. Lubricants produced by the process cover the full range of lubricant viscosities and exhibit a remarkably high VI and low pour point even at high viscosity. The molecular structure of HVI-PAO is novel, comprising the product of an essentially regular head to tail polymerization of alpha-olefin and providing an oligomer with large pendant alkyl groups on the recurring polymeric unit. The oligomer as formed is particularly characterized by containing a large proportion of terminal olefinic groups, i.e., vinylidenic groups.

Notwithstanding their generally superior properties, HVI-PAO lubricants, as well as other lubricants, are often formulated with additives, or an additive package, to enhance those properties for specific applications. The more commonly used additives include oxidation inhibitors, rust inhibitors, metal passivators, antiwear agents, extreme pressure additives, pour point depressants, detergent-dispersants, viscosity index (VI) improvers, foam inhibitors and the like, as described in Kirk-Othmer "Encyclopedia of Chemical Technology", 3rd edition Vol. 14, pp. 477–526.

Borated additive compositions can be prepared which provide superior dispersant and antioxidant activity in lubricants. In U.S. Pat. No. 4,698,169 to Andress, et al., a process is described for the production of superior additives by reacting an alkenylsuccinic compound with an arylamine and an alkanolamine, an aminomethane or a hindered alcohol, and boric acid. The alkenylsuccinic compound is typically derived as an adduct of an alkenyl compound and maleic anhydride wherein the alkenyl compound contains internal olefinic unsaturation.

U.S. Pat. No. 4,219,431 is directed to lubricant compositions containing a lubricant and a minor amount of a derivative of alkenylsuccinic anhydride which includes the reaction product of (1) an alkenylsuccinic acid, ester or anhydride and a hydroxy aromatic compound and (2) the product of reaction between (1) and an amine, (3) the reaction product of (2) and an aldehyde and (4) the reaction product of (3) and a metal salt.

U.S. Pat. No. 4,803,004 discloses dispersant additives made from an alkenyl (succinic compound by reaction with an arylamine and a hindered alcohol.

SUMMARY OF THE INVENTION

It has now been found that the unique structure of the HVI-PAO oligomer, particularly with respect to the reactivity of the vinylidinic group of that oligomer enables derivatives to be prepared which are useful as additives for lubricants. A preferred group of additives are the borated derivatives of HVI-PAO, especially the borated derivatives of maleic anhydride adducts of HVI-PAO.

Maleic anhydride adducts of HVI-PAO and their preparation are described in co-pending application Ser. No. 07/342,779, filed 25 April 1989, to which reference is made for such a description.

The maleic anhydride adduct of HVI-PAO can be reacted with amines and amino alcohols to produce a product which can be further reacted with boric acid and alkanols to produce a borated HVI-PAO product that possesses superior dispersant properties in engine oil applications. It has further been discovered that due to the unique vinylidinic content of HVI-PAO these compositions can be produced much more readily than known compositions of related character.

A particular borated reaction product useful as a lubricant additive may be made from the maleic anhydride adduct of an olefinic alpha-olefin oligomer. The oligomer (HVI-PAO) comprises the product of the oligomerization of $C_2$ to $C_{24}$ alpha-olefin feedstock (includes olefin mixtures) with a reduced valence state Group VIB metal catalyst, usually on porous support such as silica. This adduct of maleic anhydride and HVI-PAO i.e. an alkenyl succinic acid, anhydride or ester, is reacted with an aryl secondary amine, an alkanol tertiary amine such as triethanolamine, boric acid or another borate ester forming derivatives of boric acid, and an alkanol.

DETAILED DESCRIPTION OF THE INVENTION

The dispersant additives of the present invention are preferably made by contacting $C_2$–$C_{24}$ alpha-olefin with CO reduced chromium oxide catalyst on silica support under oligomerization conditions to produce an olefinic oligomer having a branch ratio less than 0.19. The oligomer is then reacted with maleic anhydride at elevated temperature to produce an alkenyl succinic acid anhydride or ester which is then reacted at elevated temperature with an amine, preferably an aryl secondary amine. The reaction product is then reacted with an alkanol tertiary amine at elevated temperature to form a hydroxy ester which is then borated by reaction with boric acid and a $C_1$–$C_{12}$ alkanol.

The olefinic oligomers or lubricants useful in the present invention in the formation of adducts with maleic anhydride include all those unsaturated HVI-PAO lubricants having 20 to 5000 carbon atoms where one or more of the unsaturated groups is allylic unsaturation. As oligomerized, HVI-PAO oligomers are mixtures of dialkyl vinylidenic and 1,2 dialkyl or trialkyl mono-olefins. In general, the novel HVI-PAO oligomers have the following regular head-to-tail structure where n can be 3 to 17:

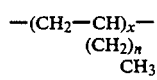

with some head-to-head connections. HVI-PAO oligomers of this type are described in U.S. Pat. Nos. 4,827,064 and 4,827,073, to which reference is made for a description of them and their preparation.

The process used to produce the HVI-PAO oligomers can be controlled to yield oligomers having weight average molecular weight between 300 and 45,000 and number average molecular weight between 300 and 18,000. Measured in carbon numbers, molecular weights range from $C_{30}$ to $C_{1300}$ and viscosity up to 750cs at 100° C., with a preferred range of $C_{30}$ to $C_{1000}$ and a viscosity of up to 500cs at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5.

Olefins suitable for use as starting material to prepare unsaturated HVI-PAO oligomers for this invention include those olefins containing from 2 to about 24 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used are preferably alpha- olefinic as for example 1-heptene to 1-hexadecene and more preferably 1-octene to 1-tetradecene, or mixtures of such olefins.

HVI-PAO oligomers of alpha-olefins have a low branch ratio of less than 0.19 and superior lubricating properties compared to the alpha-olefin oligomers with a high branch ratio, as produced in all known commercial methods.

HVI-PAO oligomers are prepared by oligomerization reactions in which a major proportion of the double bonds of the alphaolefins are not isomerized. These reactions include alpha-olefin oligomerization by supported metal oxide catalysts, such as Cr compounds on silica or other supported IUPAC Periodic Table Group VIB compounds. The catalyst most preferred is a lower valence Group VIB metal oxide on an inert support. Preferred supports include silica, alumina, titania, silica alumina, magnesia and the like.

In general the support material may be added to a solution of the metal compounds, e.g., acetates or nitrates, etc., and the mixture is then mixed and dried at room temperature. The dry solid gel is purged at successively higher temperatures to about 600° for a period of about 16 to 20 hours. Thereafter the catalyst is cooled down under an inert atmosphere to a temperature of about 250° to 450° C. and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence CrII state. Finally the catalyst is cooled down to room temperature and is ready for use.

The branch ratios used herein are defined as the ratios of $CH_3$ groups to $CH_2$ groups in the lube oil are calculated from the weight fractions of methyl groups obtained by infrared methods, published in *Analytical Chemistry*, Vol. 25, No. 10, p. 1466 (1953).

$$\text{Branch ratio} = \frac{\text{wt fraction of methyl group}}{1 - (\text{wt fraction of methyl group})}$$

To produce the HVI-PAO low molecular weight products suitable for use in the present invention the reaction is carried out at a temperature of 90°–250° C.

The following examples are presented for illustration of the preparation of HVI-PAO unsaturated oligomers used in the instant invention.

EXAMPLE 1

Catalyst Preparation and Activation Procedure 1.9 grams of chromium (II) acetate $(Cr_2(OCOCH_3)_4 2H_2O)$ (5.58 mmole) (commercially obtained) is dissolved in 50 cc of hot acetic acid. Then 50 grams of a silica gel of 8–12 mesh size, a surface area of 300 $m^2/g$, and a pore volume of 1 cc/g, also is added. Most of the solution is absorbed by the silica gel. The final mixture is mixed for half an hour on a rotavap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$ and ready for use.

EXAMPLE 2

The catalyst prepared in Example 1 (3.2 g ) is packed in a 3/8" stainless steel tubular reactor inside an $N_2$ blanketed dry box. The reactor under $N_2$ atmosphere is then heated to 150° C. by a single-zone Lindberg furnace. Pre-purified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt % | 10 | 41 | 74 | 31 |
| Viscosity, cS, at 40° C. | 208.5 | 123.3 | 104.4 | 166.2 |
| 100° C. | 26.1 | 17.1 | 14.5 | 20.4 |
| VI | 159 | 151 | 142 | 143 |

The olefin oligmer is then reacted with maleic anhydride to form an adduct which may be characterized as an alkenyl succinic anhydride. This anhydride may be converted to the corresponding acid or esters by reaction with water or an alcohol, respectively. The reaction of maleic anhydride with the olefin oligomer is described in application Ser. No. 07/342,779, filed 25 April 1979, to which reference is made for a description of the reaction and the manner in which it is carried out. The molar ratio of the maleic anhydride to the oligomer is preferably about 1:1 to obtain the desired equimolar adduct although an excess of either reactant may be removed by fractionation of the product.

The adduct formed by reaction between the maleic anhydride and the oligomer is then reacted with an amine and an alkanolamine to form an intermediate aminoester which can then be borated to form the desired dispersant additive. The preferred amines for reaction with the maleic anhydride/oligomer adduct are the secondary amines, preferably the aromatic secondary amines such as diphenylamine. Use of a secondary amine ensures the desired reaction course between the adduct, the amine and the hydroxyamine with both the amine and the hydroxyamine residues bonding to the moiety formed by ring opening of the adduct, as shown below

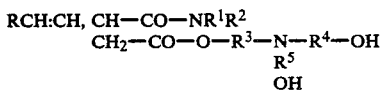

where R is an alkyl group derived from the oligomer
$R^1$, $R^2$ are aliphatic or aromatic groups derived from the amine
R,R,R, are alkylene groups derived from the hydroxyamine.

The aryl secondary amines which are preferably used have the formula $R^1R^2NH$, wherein $R^1$ and $R^2$ are alike or different comprising aromatic or alkyl groups and at least one of $R^1$ or $R^2$ is an aromatic group. The aromatic or aryl groups will generally have six to about 30 carbons atoms, comprising mono or polynuclear aromatic hydrocarbons. These aromatic hydrocarbons may contain substituent groups such as alkyl, hydroxyl, amino, sulfhydril and the like. Alkyl groups included in the aryl secondary amines can be taken from $C_1$-$C_{12}$ alkyl groups, particularly methyl, ethyl, i-propyl, n-propyl, n-butyl, i-butyl, tert-butyl and amyl. Examples of aryl secondary amines include diphenylamine, phenylnaphthylamine, dinaphthylamine, phenylbiphenylamine, methylphenylamine, ethylphenylamine, i-propylphenylamine, n-butylphenylamine, tert-butylphenylamine, i-butylphenylamine and their salts and other such amines disclosed in U.S. Pat. No. 4,803,004 as suitable for reaction with alkenyl succinic anhydrides for dispersant preparation. A preferred aryl secondary amine is diphenylamine. The amine is preferably used in a ratio relative to the adduct sufficient to achieve a substantial degree of amidation of the anhydride group. At least 0.5:1 (amine:adduct) up to 1 is preferred and generally no more than an equimolar amount should be reacted with the adduct in order to preserve sufficient carboxyl functionality for esterification.

The hydroxyamines e.g. alkanol tertiary amines useful in the present invention have the formula $HOR^3N(R^4OH)R^5OH$ where $R^3$, $R^4$ and $R^5$ are alkylene groups having 1 to 12 carbon atoms. Normally $R^3$, $R^4$ and $R^5$ will be the same and are preferably $C_2$-$C_3$ alkylenes.

The amount of hydroxyamine relative to the adduct should be sufficient to esterify at least half the residual carboxyl groups formed by ring opening of the anhydride moeity and normally 0.5:1 to 1:1 (hydroxyamine:adduct, molar) is preferred, normally about 0.75:1. The preferred alkanol tertiary amine is triethanolamine.

The neutralized amide/ester formed be reaction of the maleic anhydride adduct with the amine and the amino alcohol is then borated by reation with a borating agent and an alcohol.

The use of a lower or $C_1$-$C_4$ alkanols such as methanol, ethanol, n-propanol, i-propanol, n-butanol, i-butanol and tert-butanol is particularly preferred in order to obtain a non-gelled polymeric product with a molecular weight suitable for dissolution into lubricant basestocks, especialy when using the preferred borating agent, boric acid $H_3BO_3$. Other borating agents may, however, be used, including metaboric acid, alkyl metaborates, alkyl boroxines, boroxine boroxides or alkyl borates such as the trialkyl (methyl, ethyl, i-propyl) borates, as described in U.S. Pat. No. 4,652,387. The borating agent should be used in an amount relative to the neutralized adduct which converts free hydroxyl groups on the moiety derived from the hydroxyamine to borated ester groups. With polyfunctional borating agents such as boric acid the potential exists for high molecular weight, gel type condensation products to be produced by condensation reactions. The alkanol will, however, reduce the functionality of the borating agent sufficiently to preclude the formation of these insoluble and undesirable gel products. Thus, the amount of alkanol should be selected according to the amount and functionality of the borating agent so as to obtain a product of the desired molecular weight and viscosity. Using boric acid it has been found that the alkanol should be used in a molar ratio of about 0.75:1 (alkanol:boric acid) for products of satisfactory viscosity, but depending upon the exact materials used, more or less alkanol may be used relative to the borating agent.

The boration reaction is conveniently carried out at temperatures up to about 200° C. using a mixture of the neutralized/esterified adduct and the borating agent together, if necessary, with any alkanol to prevent gellation. The progress of the boration reaction may be monitored by the liberation of water formed in the reaction. If boric acid is used as the borating agent, additional water will be liberated at temperatures above about 105° C. by dehydration of the boric acid to metaboric acid and accordingly, allowance should be made for this in monitoring the course of the reaction. If borate esters e.g. trimethyl, triethyl or tri-i-propyl borates are used as the borating agents, the formation of the desired borated adduct will proceed by a transesterification reaction involving liberation of the more volatile lower alcohol e.g. methanol, ethanol, iso-propanol, so that the evolution of this species may likewise to used to monitor the course of the boration reaction.

The reactions by which the products in accordance with the invention are obtained can, broadly, be carried out over a wide range of conditions of from about 50° C. to about 350° C. in from about 0.5 hour to about 10 hours, depending on temperature and reactivity of the reactants, and at atmospheric or elevated pressures. The temperature of reaction can be from about 50° C. to about 350° C. and preferably is from about 100° C. to about 200° C. for the reaction between the alkenylsuccinic compound and the secondary amine. When carrying out the reaction of the amidated adduct amine with the alkanolamine, the temperature will generally be from about 100° C. to about 300° C., preferably about 50° C. to about 275° C. Times will run from about 1 hour or less to about 10 hours. As noted above, the boration will typically be carried out at an elevated temperature up to about 200° C.

In the following Examples 3–5, the preparation of the dispersant additives is described. Example 3 describes the preparation of the alkenylsuccinc anhydride adduct by reaction between HVI-PAO olefinic oligomer and maleic anhydride. In Example 4 the adduct is converted to an amide of succinic acid and neutralized with an alkanolamine. This product is borated in Example 5 with boric acid and butanol in the presence of an aromatic solvent to form the borated ashless dispersant.

EXAMPLE 3

Preparation of Alkenyl Succinic Anhydride Adduct 2400 gms (2.20 moles) of polydecene HVI-PAO prepared via chrome/silica catalysis having a bromine number of 14.6 and a calculated molecular weight of 1090 is reacted at 254° C. with 235 gms (2.40 moles) of maleic anhydride for 6 hours. The batch after 6 hours is vacuum stripped at 175° C. and 10mm to remove unreacted maleic anhydride. The yield after stripping is 2612 gms. The acid number run under anhydrous conditions is 43.5.

EXAMPLE 4

Amidation—Neutralization 1290 gms of the above polydecene adduct (1.0 mole) is reacted with 169 gms (1.0 mol) of diphenylamine for 3 hours at 160° C.. After cooling 112 gms (0.75 mol) of triethanolamine is added and the mixture stirred for 5 hours at 225° C. for acid value 2.0.

EXAMPLE 5

Boration

To 1560 gms of the above is added 386 gms of butanol and 309 gms of toluene together with 270 gms of boric acid (4.37 mol). The mixture is refluxed for 7 hours at 150° C. making 165 gms of water. The product is subsequently stripped and filtered. The overall yield is 1910 gms. The product upon analysis contained 2.25% boron with a total acid and base number of 44.0 and 27.0 respectively.

The properties of a PAO synthetic lubricant containing about 33% of an additive package in which the dispersant component of the additive package has been replaced with the product of this invention prepared as described above are given in Table 1 below.

TABLE 1

| KV @ 100° C. | 9.5 |
|---|---|
| KV @ 40° C. | 53 |
| CCS @ −25 | 23.1 |
| MRV @ −30 | 65/<35 |
| Phosphorous, wt % | 0.12 |
| Zinc, wt % | 0.11 |
| Calcium, wt % | 0.23 |

In Table 2 below, the properties of three different borated ashless dispersants are compared. The difference in the dispersants is primarily in the composition of the alkenyl group of the alkenylsuccinic anhydride. In Column A the anhydride was prepared from polyisobutylene prepared by conventional catalysis. In Column B the anhydride was prepared from 1-decene HVI-PAO oligomer. In Column C the anhydride was prepared from 1-decene oligomer which was oligomerized using conventional PAO Lewis acid catalysis. It can be seen from these results that the conversion of oligomer to useful adduct is substantially higher for the product of this invention (Column B), than for dispersant prepared from conventional oligomers. The borated dispersant from the HVI-PAO oligomer is, moreover, more highly borated and has a higher Total Base Number (TBN).

TABLE 2

| ASA | A | B (HVI-PAO) | C (PAO) |
|---|---|---|---|
| Oligomer | polyisobutylene | polydecene | polydecene |
| Type olefin | i-butylene | 1-decene | 1-decene |
| MW | 1300 | 1090 | 1300 |
| % Conversion | 75 | 95 | 46 |
| Borated Dispersant-ASA/DPA/TEA (1.0/1.0/0.75) | | | |
| TBN | 4.6 | 24.7 | 8.2 |
| % Boron | 1.4 | 2.47 | 1.79 |
| % Active | 60.0 | 100 | 100 |

What is claimed is:

1. The borated reaction product produced by reacting
   (i) the maleic anhydride adduct of an olefinic alpha-olefin oligomer, said oligomer comprising oligomerizing $C_2$ to $C_{24}$ alpha-olefin in the presence of a reduced Group VIB metal catalyst to produce an olefinic oligomer having a branch ratio of less than 0.19, with
   (ii) a secondary amine;
   (iii) an alkanol amine; and
   (iv) a borating agent.

2. The reaction product of claim 1 wherein said oligomer has a branch ratio of less than 0.19, weight average molecular weight between 300 and 45,000, number average molecular weight between 300 and 18,000, molecular weight distribution between 1 and 5 and pour point below −15° C.

3. The reaction product of claim 1 wherein the secondary amine has the formula $R^1R^2NH$, wherein $R^1$ and $R^2$ are alike or different comprising aromatic or alkyl groups and at least one of $R^1$ or $R^2$ is an aromatic group.

4. The reaction product of claim 1 wherein said alkanol amine has the formula $(HOR)3N$ where R is an alkylene group having 1 to 12 carbon atoms.

5. The reaction product of claim 1 wherein said secondary amine comprises diphenyl amine and said alkanol- amine comprises triethanolamine.

6. A process for the preparation of borated lubricant additive, comprising:
   (i) oligomerizing $C_2$–$C_{24}$ alpha-olefin in the presence of a reduced Group VIB metal catalyst to produce olefinic oligomer having a branch ratio less than 0.19;
   (ii) reacting said oligomer with maleic anhydride at elevated temperature to produce an alkenyl succinic anhydride;
   (iii) reacting said alkenyl succinic anhydride with a secondary amine and an alkanolamine;
   (iv) reacting step (iii) reaction product with a borating agent to produce a borated reaction product useful as a lubricant additive.

7. The process of claim 6 wherein step (iii) and step (iv) are carried out under temperature conditions between about 50° C. and 350° C.

8. The process of claim 6 in which the secondary amine has the formula $R^1R^2NH$, wherein $R^1$ and $R^2$ are alike or different comprising aromatic or alkyl groups and at least one of $R^1$ or $R^2$ is an aromatic group.

9. The process of claim 8 in which alkanol amine has the formula $(HOR)3N$ where R is an alkylene group having 1 to 12 carbon atoms.

10. The process of claim 6 in which the secondary amine comprises diphenyl amine and said alkanol-amine comprises triethanolamine.

11. The process of claim 6 wherein said alpha-olefin comprises 1-decene, said secondary amine comprises diphenyl amine and said alkanolamine comprises triethanolamine.

12. The process of claim 6 wherein said alkenyl succinic anhydride and said secondary amine are reacted at a mole ratio of about 1:1.

13. A process according to claim 6 in which the boration is carried out in the presence of a monohydric alkanol.

14. A process according to claim 13 in which the alkanol comprises a $C_1$–$C_4$ alkanol.

15. A process according to claim 13 in which the borating agent comprises boric acid or metaboric acid.

16. A process according to claim 13 in which the borating agent comprises a trialkyl borate.

17. A process according to claim 6 in which the alpha-olefin comprises 1-decene.

18. A process according to claim 6 in which the catalyst comprises reduced chromium on a porous support.

19. A process according to claim 18 in which the support comprises silica.

20. A process according to claim 18 in which the chromium is CO-reduced chromium.

* * * * *